United States Patent [19]

Miyagishi et al.

[11] Patent Number: 5,069,069
[45] Date of Patent: Dec. 3, 1991

[54] MOISTURE-SENSITIVE ELEMENT FOR MOISTURE SENSORS

[75] Inventors: Tetsuya Miyagishi, Fujisawa; Toru Abe, Yokohama; Takaaki Kuroiwa, Odawara, all of Japan

[73] Assignee: Yamatake-Honeywell Co., Ltd., Tokyo, Japan

[21] Appl. No.: 515,096

[22] Filed: Apr. 26, 1990

[30] Foreign Application Priority Data

Apr. 26, 1989 [JP] Japan ................................ 1-104594
Apr. 27, 1989 [JP] Japan ................................ 1-105871

[51] Int. Cl.$^5$ ........................ H01G 5/20; G01N 25/64
[52] U.S. Cl. .................................... 73/335; 73/29.05; 361/286
[58] Field of Search ................... 73/335, 29.05; 338/35; 361/286

[56] References Cited

U.S. PATENT DOCUMENTS

| | | | |
|---|---|---|---|
| 4,473,813 | 9/1984 | Kinjo et al. | 73/335 X |
| 4,520,341 | 5/1985 | Miyoshi et al. | 73/335 X |
| 4,528,543 | 7/1985 | Miyoshi et al. | 338/35 |
| 4,642,601 | 2/1987 | Sugawara et al. | 338/35 |
| 4,681,855 | 7/1987 | Huang | 338/35 X |
| 4,761,710 | 8/1988 | Chen | 361/286 |
| 4,920,451 | 4/1990 | Sakai et al. | 361/286 |
| 4,965,698 | 10/1990 | Thoma et al. | 361/286 |

Primary Examiner—Hezron E. Williams
Assistant Examiner—Joseph W. Roskos
Attorney, Agent, or Firm—Whitham & Marhoefer

[57] ABSTRACT

A moisture-sensitive element comprising a moisture-sensitive film which consists of a polymer (such as a polymer in which polyethersulfon is a principal component) whose water sorption amount is between 10 and 40 mg/g at a temperature of 30° C. and a relative humidity of 90% RH. The temperature-sensitive element has a low temperature dependency, a small hysteresis and a quick response and accordingly can be employed in a wide range of temperature as well as in a severe condition such as high humidity, high temperature, cyclically fluctuating humidity, low humidity, moisture condensation, water dipping and so on.

19 Claims, 6 Drawing Sheets

FIG. 1
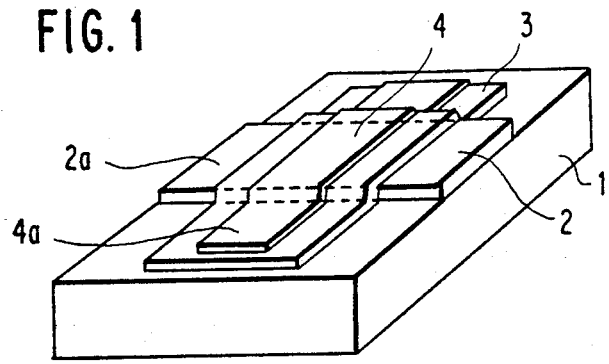
FIG. 2
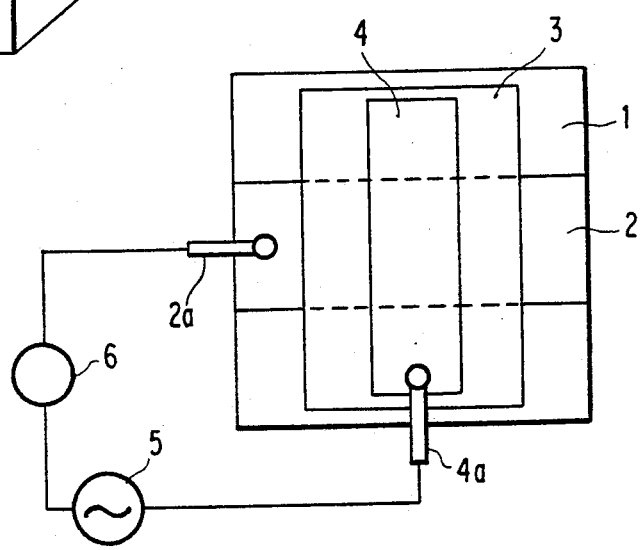
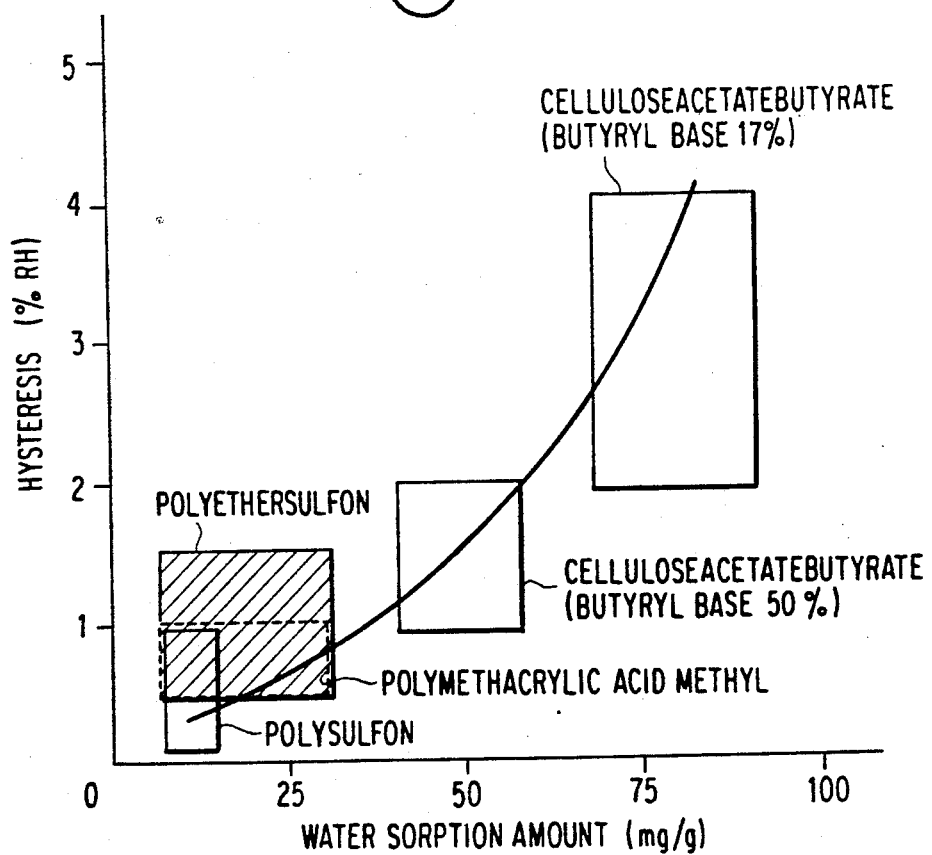
FIG. 3

FIG. 10

| Material | Water Sorption Amount (mg) | Hysteresis (%RH) | Moisture Sensitivity Characteristic (C90/C10) |
|---|---|---|---|
| Polysulfon | 10 - 15 | 0.2 - 1.0 | 1.05 - 1.08 |
| polyethersulfon | 10 - 30 | 0.5 - 1.5 | 1.12 - 1.17 |
| polyetherimide (PEI) | 22 | 0.6 | 1.10 |
| Polybenzoimidal | 22 | 0.6 | 1.10 |
| Polyether | 17 | 0.4 | 1.08 |
| Polyimide (PI) | 22 | 0.6 | 1.10 |
| Polyamideimide | 22 | 0.6 | 1.10 |
| Polyphenileneoxide | 5 | 0.2 | 1.03 |
| Polycarbonate | 28 | 0.7 | 1.12 |
| Polyallylete | 22 | 0.6 | 1.10 |
| Polymethacrylic acid methyl | 32 | 0.9 | 1.14 |
| Polybutyleneterephthalete (PBT) | 7 | 0.2 | 1.04 |
| Polyeleneterephthalate (PFT) | 5 | 0.2 | 1.03 |
| Polyetheretherketone | 15 | 0.4 | 1.07 |
| Polyetherketone | | Data not available | |
| Polyacetal | 28 | 0.7 | 1.12 |

MOISTURE-SENSITIVE ELEMENT FOR MOISTURE SENSORS

BACKGROUND OF THE INVENTION

1. Field of the Invention

This invention relates to moisture responsive sensors, and more particularly to the use in such sensors of an organic polymer film with a low hydrophylic characteristic as a moisture-sensitive element.

2. Description of the Prior Art

Prior art organic polymer moisture-sensitive elements use an organic polymer such as celluloseacetatebutyrate, cellulloseacetatepropyonate, polyimide, or polyimideamide as a moisture-sensitive materials and utilizes an electrical capacitance change in a moisture-sensitive film formed of such moisturesensitive material to detect humidity, as disclosed in Published Japanese Patent Application No. 62-88951.

Such moisture-sensitive elements described above are highly hydrophilic and accordingly a large amount of water is absorbed by such elements. The absorbed water is strongly bonded to the polymer and remains in the element. For this reason, if the element is used at a high temperature and high relative humidity atmosphere, e.g. at 40° C. and 90% for a long time, the output value thereof drifts or long-term stability is damaged.

Also, in the highly hydrophilic prior art organic polymer elements a moisture-sensitivity characteristic difference (hysteresis) between moisture absorption and desorption processes is decreased at a low-temperature side and increased at a high-temperature side, thereby causing delay in sensor response.

Further, if such a prior art element is used in a low humidity atmosphere for a long time the hysteresis will become larger. Even in a favorable atmosphere, a continuous use of the element for a long time will cause its capacitance ratio to be change, thus resulting in deteriorating of long-term stability of the element.

Furthermore, moisture condensation or water dipping will also cause the output of the element to drift.

For example, celluloseacetatebutyrate (hereinafter simply referred to as "CAB") having 17% of butyryl base typically used as moisture-sensitive material in the above-mentioned type of conventional moisture-sensitive element has a water sorption amount of approximately 70–90 mg/g in an equilibrated condition at a temperature of 30° C. and a relative humidity of 90% RH.

Such moisture-sensitive element having a moisture-sensitive film made of CAB presents 2–4% RH of hysteresis (difference in moisture sensitivity characteristic between moisture absorption and desorption processes) at about 25° C. and at measuring intervals of 5 minutes. Therefore, it is not possible to reduce the hysteresis to less than 1% RH, as considered ideal. Also, the hysteresis is temperature dependent and increased by 2–3% RH at about 40° C. compared with the value derived at 25° C. if other conditions are the same.

Further, if the above-mentioned type of moisture-sensitive element is left in the same atmosphere for a long time, the effect of humidity to which the element has previously been exposed causes a change in the hysteresis and the moisture sensitivity characteristic. Specifically, if the element is left, e.g., at a relative humidity of 11% RH and a room temperature for a long time, the hysteresis is increased from an initial value of 2% RH to 4–6% RH. If the same element is left at a relative humidity of about 84% RH and a room temperature for a long time, the hysteresis is decreased from the initial value, i.e. 2% RH to about 1% RH. However, with respect to the moisture sensitivity characteristic, the output is increased by 5–7% RH in a relative humidity ranging from 10 to 90% RH, that is, a drift occurs in the output. Further, a ratio of an electrical capacitance value at a relative humidity of 90% RH to that at a relative humidity of 10% RH ($C_{90}/C_{10}$) is fluctuated while the element is used for a long time.

Further, a high temperature and high humidity environment, moisture condensation, water dipping, a temperature and humidity cycle and so on also cause the moisture sensitivity characteristic of the element to drift largely in the positive direction.

These problems are caused by the fact that a water sorption amount (water adsorption ratio) of the moisture-sensitive material employed in the above-mentioned conventional moisture-sensitive element is too large to be an ideal capacitance type or impedance type moisture-sensitive element. Thus, interaction of water molecules absorbed in the moisture-sensitive material causes a change in response of the element and an equilibrated water sorption amount in a measured humidity atmosphere, thereby incurring a drift in the output of the element.

OBJECTS AND SUMMARY OF THE INVENTION

In view of the foregoing problems, it is a principal object of the present invention to provide a moisture-sensitive element which has a low temperature dependency and accordingly can be employed in a wide range of temperature from a high temperature to a low temperature.

It is another object of the present invention to provide a moisture-sensitive element which shows a small hysteresis and a quick response in a usable range from a high temperature to a low temperature and from a high humidity to a low humidity.

It is a further object of the present invention to provide a moisture-sensitive element which is capable of generating a stable output in any severe condition such as high humidity, high temperature, cyclically fluctuating humidity, low humidity, moisture condensation, water dipping and so on.

To achieve the above objects, the present invention provides a moisture-sensitive element comprising a moisture-sensitive film which is made of a polymer material, the water sorption amount of which is in a range between 10 and 40 mg/g at a temperature of 30° C. and a relative humidity of 90% RH.

Specifically, in the preferred specific embodiment the present invention provides a moisture-sensitive element comprising a moisture-sensitive film which comprises a polymer including polyethersulfon as a principal component.

The present invention also provides a moisture-sensitive element comprising a moisture-sensitive film which is formed of polyethersulfon and annealed at a temperature ranging between 160° C., and 240° C.

These and other objects, features and advantages of the present invention will become apparent from the following detailed description of the preferred embodiments with reference to the accompanying drawings.

BRIEF DESCRIPTION OF THE DRAWINGS

FIG. 1 is a perspective view showing an embodiment of a moisture-sensitive element according to the present invention;

FIG. 2 is a top plan view of the moisturesensitive element shown in FIG. 1;

FIGS. 3, 3a and 3b are graphs showing the hysteresis, temperature dependency of moisturesensitive elements using polyethersulfon and polysulfon;

FIG. 10 is a chart showing the hydrophilic characteristics of certain suitable materials.

DETAILED DESCRIPTION OF THE PREFERRED EMBODIMENTS

Figure 3A:
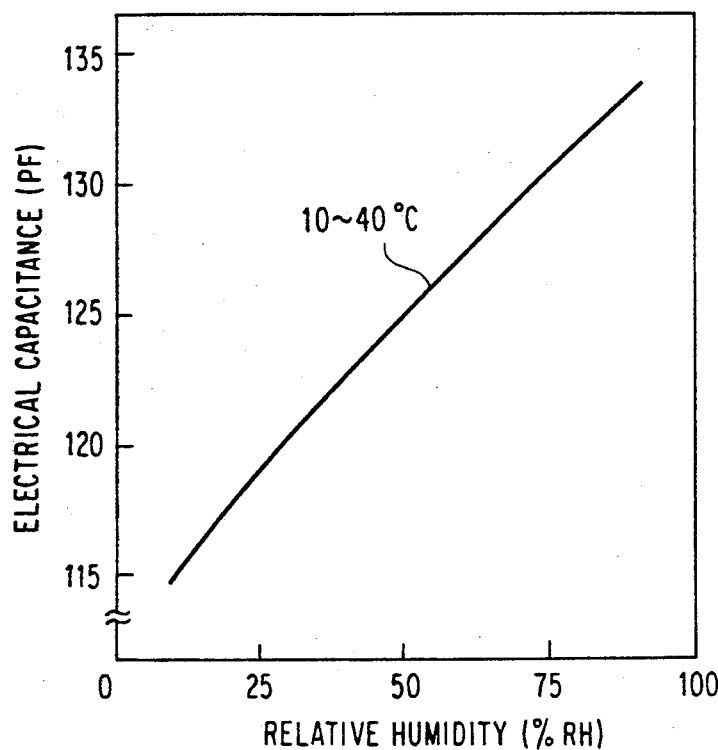

A first embodiment of a moisture-sensitive element according to the present invention will hereinafter be described with reference to FIGS. 1 and 2.

In these drawings, an insulating substrate 1 made, e.g., of alumina, glass, thermally oxidized silicon or the like, is provided, and on the upper surface thereof a lower electrode 2 made e.g. of platinum is formed. Also, a moisture-sensitive film 3 is stacked on and across the lower electrode 2. In a preferred specific embodiment of the invention this film 3 is made of a polymer moisture-sensitive material whose principal component is polyethersulfon (hereinafter referred to a "PES") or polysulfon.

An upper electrode 4 made, e.g. of gold, is formed on the moisture-sensitive film 3. In other words, the moisture-sensitive film 3 is sandwiched between the lower and upper electrodes 2, 4 and preferably extends before then. Leads 2a, 4a couple the lower and upper electrodes 2, 4, respectively to an a.c. source 5 and a suitable meter 6 to detect a change in an electric capacitance in response to changes in the amount of moisture adsorbed by the film 3 as a result, for example, of changes of the atmosphere to which the moisture-sensitive film 3 is exposed.

A specific manufacturing process of the abovementioned moisture-sensitive element will be explained below.

First, 10–40 grams of PES powder is dissolved in a mixed solvent typically made up of 20 milliliters of dimethylformamide, 80 milliliters of cyclohexanon and 25 milliliters of methylethylketone to provide PES solution. Next, this PES solution is coated on the lower electrode 2 formed on the insulating substrate 1 by a spin coating method and then dried in a nitrogen atmosphere at room temperature to form the moisture-sensitive film 3 having a thickness ranging from 0.5 μm to 5 μm. The spinner typically rotates at a speed of 500–5000 r.p.m.

After this drying operation at room temperature, the element is annealed at a temperature between 160° C. and 240° C. for at least one hour. Next, the upper electrode 4 having a thickness ranging from 50 to 1000 A is deposited on the insulating substrate 1 having the moisture-sensitive film 3 thus formed thereon, e.g. by a vapor deposition method or a sputtering method. The metal used for the electrode 4 is not limited to gold, and any anti-corrosion metal such as palladium, platinum, chrome or the like may be used in place of gold. The lower electrode 2 is formed on the insulating substrate 1 by depositing platinum by a vapor deposition, sputtering method or the like in a thickness of 1000–10000 A.

Since the moisture-sensitive film 3 is formed, as mentioned above, by dissolving PES powder in a solvent mixture made up of dimethylformamide, cyclohexanon and methylethylketone, coating the solvent in a small amount on the lower electrode previously formed on the insulating substrate 1, and drying the coated solvent at room temperature, the solvent is evaporated to leave a thin polymer in a high density, thereby making it possible to largely reduce a water sorption amount to 0.2–0.4 wt % and also the hysteresis.

A similar effect can be produced if a single solvent having a strong polarity such as dimethylformamide, cyclohexanon and methylethylketone is used in place of the above-mentioned solvent mixture.

In a second preferred embodiment of the present invention, the moisture-sensitive film 3 is formed of polysulfon in place of the above-mentioned PES. In this case, an annealing process is carried out at a temperature between 140° C. to 200° C. for at least one hour, after a drying process at room temperature, to thereby produce the same effect as the first embodiment.

The polysulfon and PES respectively have a constitutional formula as shown below:

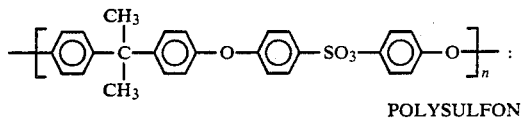

POLYSULFON

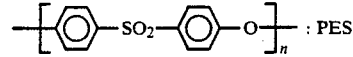 : PES

In comparison of these two materials with each other, the polysulfon has C(CH3)2 while the PES has SO2, at the corresponding position, so that the polysulfon has a water sorption amount and a sensitivity ⅓ as much as the PES. However, such reductions of the water sorption amount and sensitivity will not cause any problem in practice, and it is therefore possible to provide a moisture-sensitive element made of polysulfon which has a low temperature dependency and low drift in its output even in a high-temperature and high-humidity condition.

Figure 3B:
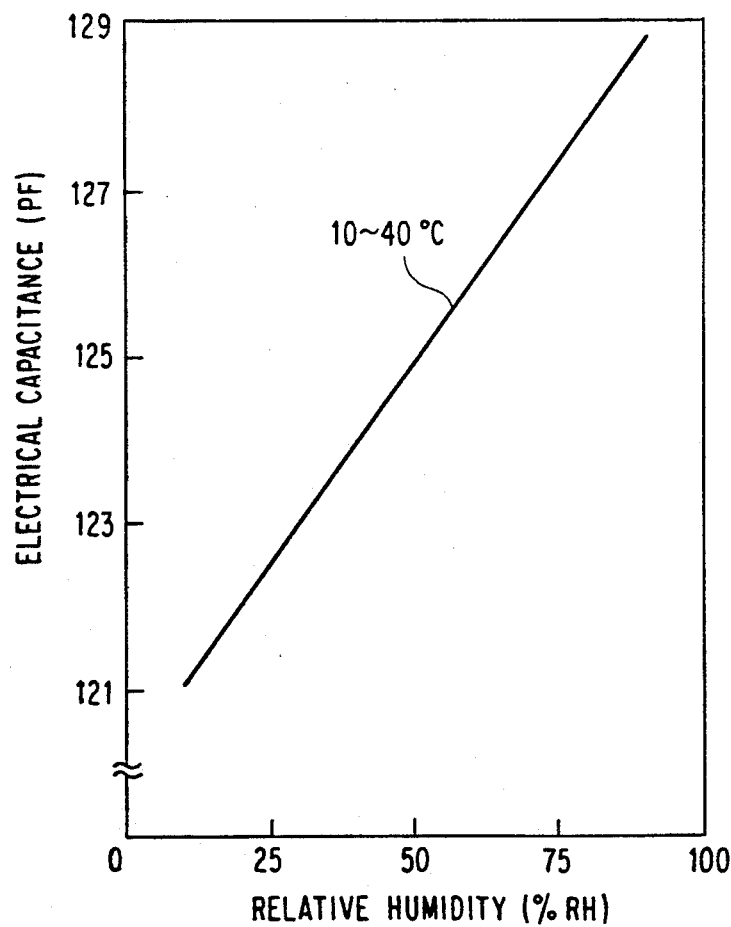

FIGS. 3a and 3b are respectively a graph showing the relationship between electrical capacitance and relative humidity of the moisture-sensitive film 3 of the PES and polysulfon embodiments. It should be noted that the measurements of the both moisture-sensitive films were made at a frequency of 100 KHz and a temperature of 10° C., 25° C. and 40° C. by means of a LCZ meter. The measured points for each temperature fall along the same line in the respective graphs. Thus as indicated in these drawings, satisfactory moisture-sensitive characteristics with quite low temperature dependency were provided. Since a detected output does not suffer from fluctuation due to temperature, a temperature compensation circuit is not necessary. Also, FIGS. 3a, 3b shows a satisfactory result that the hysteresis is below 1% RH when measured approximately two minutes after a constant humidity bath becomes stable.

Figure 4:
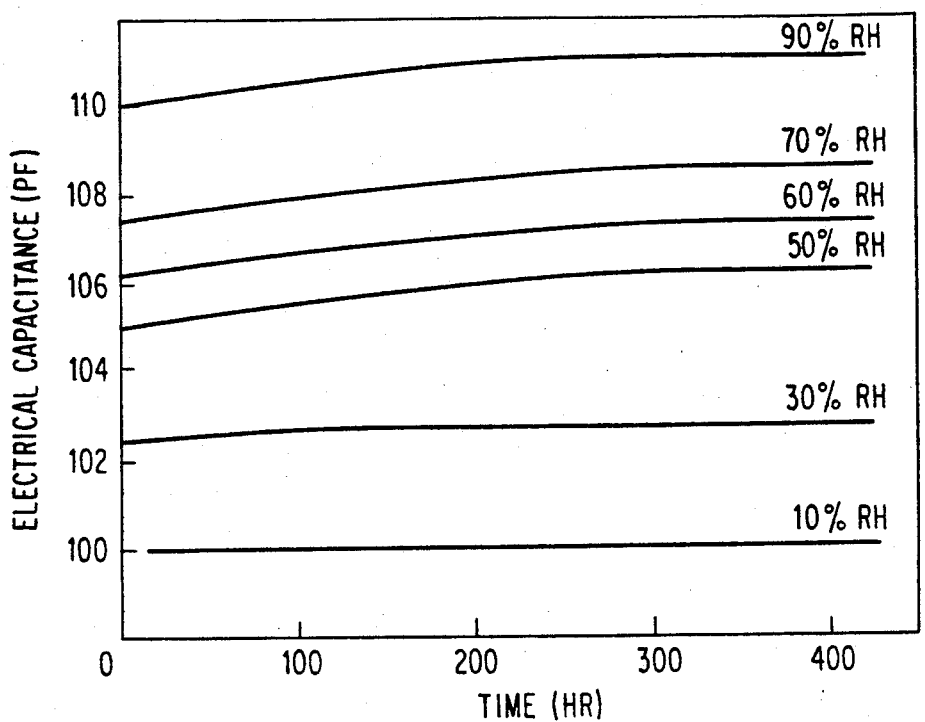
FIG. 4 is a graph showing a moisture sensing characteristic of the moisture-sensitive element according to the present invention.
Figure 5:
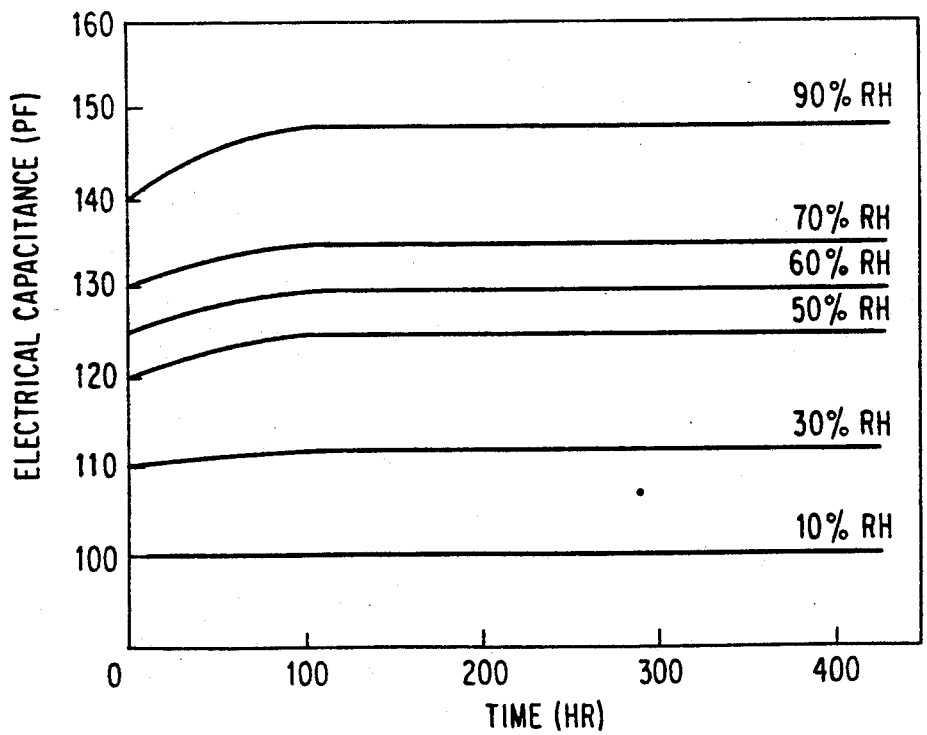
FIG. 5 is a graph showing a moisture sensing characteristic of a prior art moisture-sensitive element.

FIG. 4 shows the relationships between elapsed time and drift amounts in outputs from a moisture-sensitive element manufactured according to the present invention at a relative humidity of 10, 30, 50, 60, 70 and 90% RH. FIG. 5 shows the same characteristics derived by a moisture-sensitive element employing a conventional celluloseacetatebutyrate as a moisture-sensitive material which was left in the same condition as the above for purpose of comparison. As is apparent from these drawings, the moisture-sensitive element of the present invention provides a stable moisture-sensitive characteristic with less drift in comparison with the conventional moisture-sensitive elements shown in FIG. 5. Also, the hysteresis is below 1% RH when measured approximately two minutes after a constant humidity bath becomes stable. From these measurement results, it can be said that the moisture-sensitive element of the present invention has good reproductivity and a stable capacitance ratio even if it is used in a high temperature and high humidity atmosphere or even if it is left in the same atmosphere for a long time. Further, it is appreciated that the moisture-sensitive element can reversibly recover its initial characteristic when it is left in a high temperature and high humidity atmosphere and then brought back to a room temperature atmosphere.

In the above embodiments, a sandwich type moisture-sensitive element is explained by way of example, however, the present invention is not limited to this type. The same effects as mentioned above can be produced if the present invention is applied to a comb type moisture-sensitive element which has a pair of comb-type thin film electrodes formed on an insulating substrate opposite to each other and a moisture-sensitive film covering the comb-type thin film electrodes.

Further, in the above embodiments, humidity is detected on the basis of an electrical capacitance change with respect to a relative humidity of the moisture-sensitive film. Alternatively, humidity can be detected on the basis of an impedance change with respect to the relative humidity.

The moisture-sensitive film in the above embodiments can also be suitably employed for a moisture sensor in which the moisture-sensitive film is formed on a quartz vibrator and which detects humidity on the basis of a resonance frequency offset caused by water absorption of the moisture-sensitive film as well as a moisture sensor in which the moisture-sensitive film is formed on a surface elastic wave element and which detects humidity on the basis of a change in speed of a wave passing through the surface elastic wave element.

The moisture-sensitive film 3 of FIGS. 1 and 2 may be made of polymer moisture sensitive materials other than polysulfon and PES. Suitable polymer films having a low hydrophilic characteristic include; polyetherimide, polybenzimidal, polyether, polyimide, polyamideimide, polyphenileneoxide, polycarbonate, polyallylete, polymethacrylic acid methyl, polyacrylonitrile, polybutyleneterephthalete, polytheleneterephthalete, polyetheretherketone, polyacetal or the like. FIG. 10 is a chart showing the hydrophilic characteristics of these materials.

The hydrophilic properties of these materials can be determined by coating the respective materials on a quartz vibrator in a thickness of approximately 10 $\mu m$ or less to form moisture-sensitive films. The moisture-sensitive films are then located in a constant humidity atmosphere to measure respective water sorption amount at about 30° C. based on a change in an oscillating frequency of the quartz vibrator.

Each of the above-mentioned polymer materials is also coated on the lower electrode 2 deposited on the insulating substrate 1 in a thickness of about 10 $\mu m$ or less to form the moisture-sensitive film 3 on which the upper electrode 4 is formed as mentioned above. With this structure, the relationship between the electrical capacitance ratio and the relative humidity is measured at about 30° C. The same measurements were also performed with the moisture-sensitive film 3 made of conventionally used celluloseacetatebutyrate. It should be noted that a water sorption amount and moisture sensitivity characteristic subtly fluctuate due to a forming method of the polymer film, a thickness of the film, an annealing method, a forming method of the upper electrode 4 and so on.

It was found, from the results of the above measurement, that the celluloseacetatebutyrate film (including 17% of butyryl base) has a water sorption amount of 70-90 mg/g (at 30° C. 90% RH), a hysteresis of 2-4% RH and an electrical capacitance ratio ($C_{90}/C_{10}$) of 1.21-1.42, while the celluloseacetatebutyrate film (including 50% of butyryl base) has a water sorption amount of 40-60 mg/g, a hysteresis of 1-2% RH and an electrical capacitance ratio ($C_{90}/C_{10}$) of 1.10-1.20. With a polymethacrylic acid methyl film, a satisfactory result was obtained, where a water sorption amount is 10-30 mg/g, a hysteresis 0.5-1.0% RH and $C_{90}/C_{10}$ 1.06-1.15. Good results were also obtained by a polyethersulfon film and a polysulfon film. The former has a water sorption amount of 10-30 mg/g, a hysteresis of 0.5-1.5% RH and $C_{90}/C_{10}$ of 1.12-1.17 while the latter has a water sorption amount of 10-15 mg/g, a hysteresis of 0.2-1.0% RH and $C_{90}/C_{10}$ of 1.05-1.08.

Figure 9:
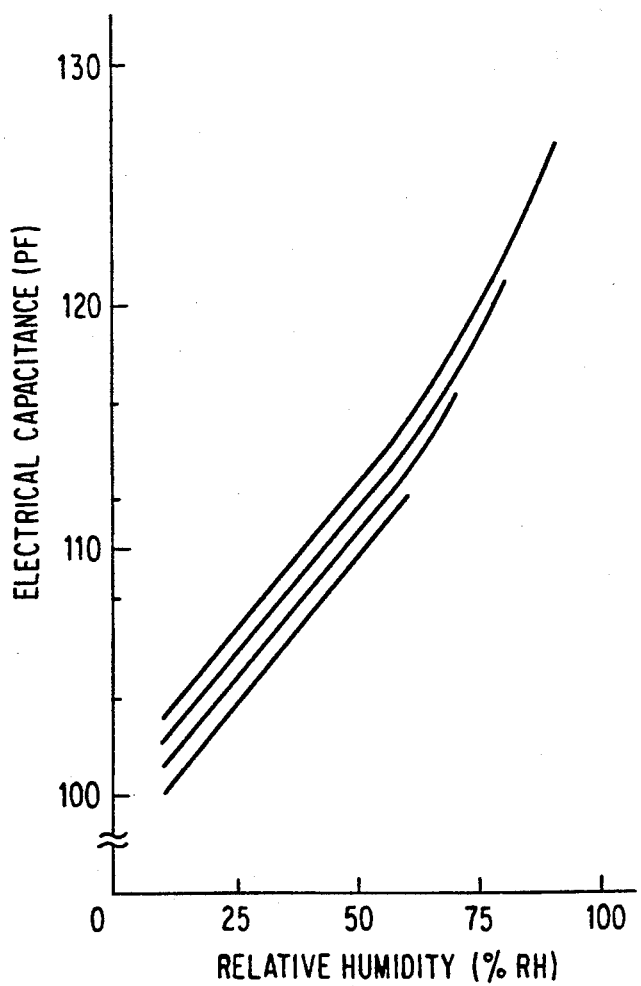
FIG. 9 is a graph showing the moisture sensitivity characteristic of a conventional moisture-sensitive element (CAB including 17% of butyryl base).

Based upon these measurement results we have determined that the amount of water molecules existing in a polymer material causes a large change in the moisture sensitivity characteristic. Specifically, and with reference to FIG. 9 in which the parallel lines in the graph show results of four measurements performed with CAB at relative humidity of 10-60-10% RH, 10-70-10% RH, 10-70-10% RH, 10-80-10% RH, and 10-90-10% RH, respectively. They should be superimposed on each other, however, they are drawn in parallel such that each result can be clearly shown. They show how the hysteresis and the linearity vary when the relative humidity is changed as mentioned above in a relative humidity range below 60% RH, the water sorption amount is 35-40 mg/g and therefore the hysteresis is 0.3-0.4% RH, where the linearity of the moisture sensitivity characteristic is quite satisfactory. However, in a relative humidity range above 60% RH, the water sorption amount exceeds 40 mg/g, whereby interaction occurs among water molecules and therefore the hysteresis is gradually increased. For example, when measurements were performed at a relative humidity of 10% RH, 70% RH and 10% RH, respectively, a maximum water sorption amount was 40-45 mg/g and the hysteresis 1.2–1.5% RH. Meanwhile, when measurements were performed at a relative humidity of 10% RH, 80% RH and 10% RH, respectively, a maximum water sorption amount was 50–55 mg/g and the hysteresis 1.5–2.1% RH. It can be seen from these results that the hysteresis becomes larger as the water sorption amount is increased. Such larger hysteresis causes the linearity of the sensor output to be deteriorated.

Figure 6:
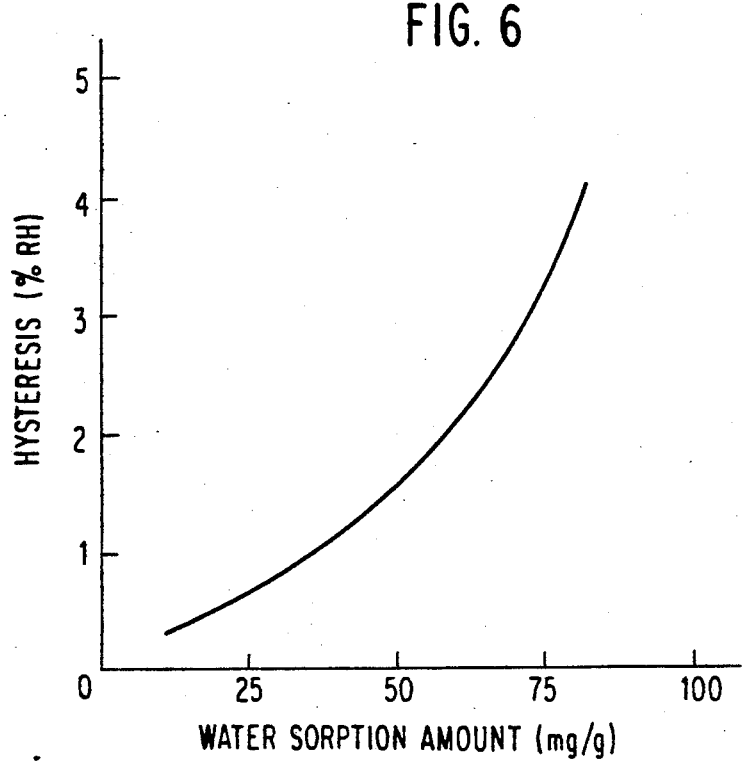
FIG. 6 is a graph showing the relationship between the water sorption amount and the hysteresis of the moisture-sensitive element of the present invention.
Figure 7:
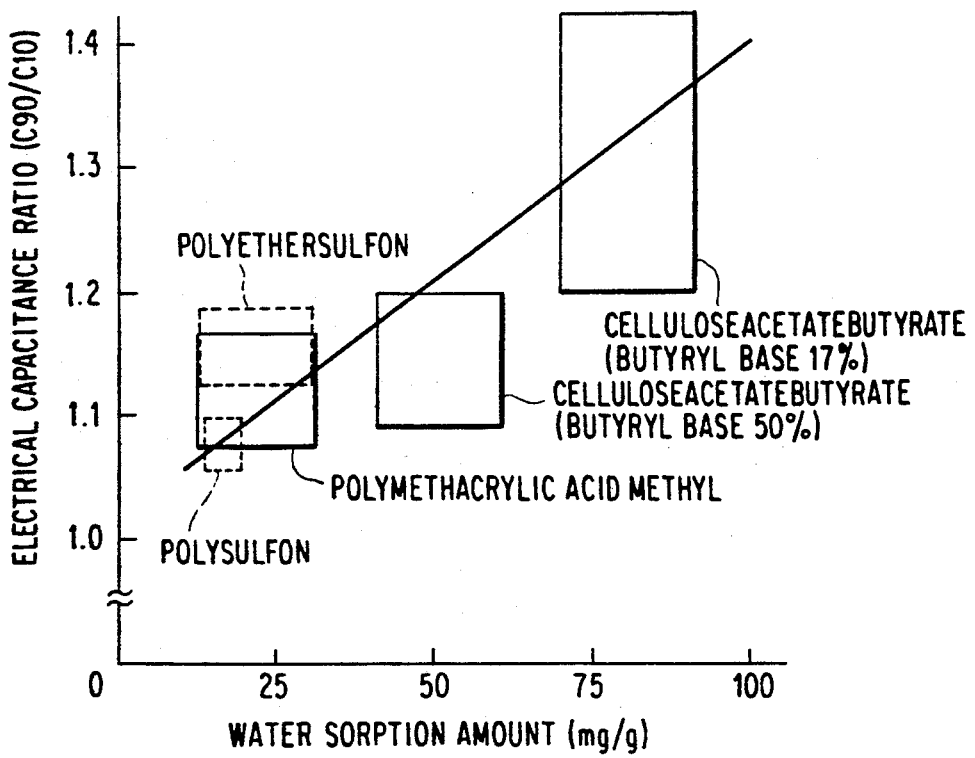
FIG. 7 is a graph showing the relationship between the water sorption amount and the capacitance ratio of a moisture-sensitive element of the present invention.
Figure 8:
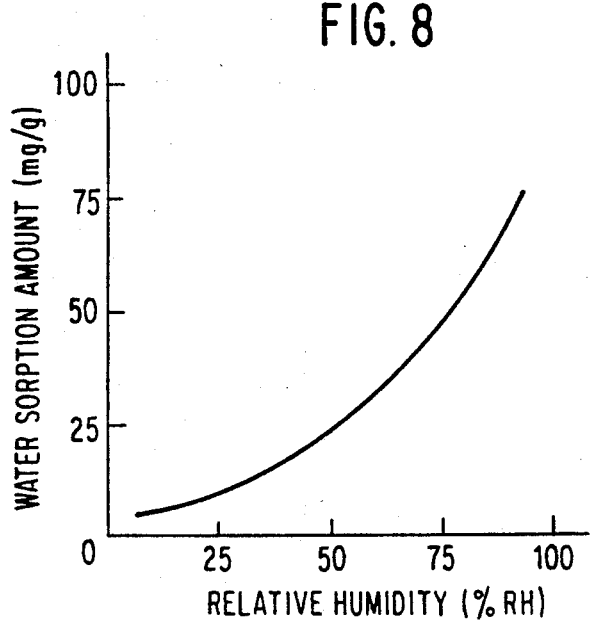
FIG. 8 is a graph showing the relationship between the water sorption amount and the relative humidity of a conventional moisture-sensitive element (CAB including 17% of butyryl base)

From our above stated results we have established that there is a close correlation between the water sorption amount of a polymer material and its moisture sensitivity characteristic. If the hysteresis is expected to be, e.g., below 1% RH, the water sorption amount should be not more than 40 mg/g. The graphs of FIGS. 6, 7 and 8 were obtained with five of the materials stated in the specification; celluloseacetatebutyrate (including 17% of butyryl base), celluloseacetatebutyrate (including 50% of butyryl base), polyethersulfon, polymethacrylic acid methyl, and polysulfon. The water sorption amount and the hysteresis subtly fluctuate due to a polymer film forming method, an annealing method and a forming method of the upper electrode. Possible range of the water sorption amount and the hysteresis of the respective materials are indicated by rectangles in the attached FIG. 3. As can be seen, the curve on FIG. 3 is a combination of possible ranges of the water sorption amount and the hysteresis of the five above-mentioned materials. FIGS. 6 and 7 were made in the same manner as FIG. 3. Incidentally, when a moisture-sensitive element as shown in FIGS. 1 and 2 is made of a polymer material having a water sorption amount of 10–40 mg/g at a relative humidity of 90% RH, its capacitance ratio ($C_{90}/C_{10}$) is 1.05–1.2.

For use in industrial applications the moisture-sensitive film should be useful over a range from $-30°$ C. to $+100°$ C. Films which have a thermal defection temperature under load above 120° C., or a resistance to heat temperature above 100° C. are suitable for such industrial applications. The polymers of this invention meet one or both of these criteria.

The polymer films of this invention are particularly well suited for use in a capacitance type oscillator. In such oscillators, a voltage of $\pm 1.5$–5.0 volts is applied across the moisture-sensitive element. Since a polymer film employed in the element has a thickness of 0.5–10 μm, a dielectric breakdown strength of more than 14 KV/mm, is required to allow the polymer film to bear such voltage.

Further, since a polymer is not an ideal insulating material, a parallel resistance exists in proportion to the volume resistivity. If the volume resistivity is below $10^{14}$ Ω-cm, the parallel resistance is also too small to achieve oscillation in the oscillating circuit. The polymer materials of this invention satisfy the requirements.

Since many changes could be made in the above construction and many apparently widely differing embodiments of the present invention could be made without departing from the scope thereof, it is intended that all matter contained in the above description or shown in the accompanying drawings shall be interpreted as illustrative and not in a limiting sense.

We claim:

1. A sensor for moisture in an atmosphere comprising in combination;
    a film composed principally of a polymer with a water sorption capacity in a range between 10 and 40 milligrams of water per gram of polymer at a temperature of 30° C. and a relative humidity of 90% RH,
    means for sensing a change in a characteristic of said film which change is a function of the moisture adsorbed by said film.

2. A sensor for moisture in an atmosphere as recited in claim 1 wherein said characteristic is the electrical capacitance of said film.

3. A sensor for moisture in an atmosphere as recited in claim 1 wherein said polymer is selected form the group consisting of polyethersulfon and polysulfon.

4. A sensor for moisture in an atmosphere as recited in claim 3, wherein said polymer is polyethersulfon annealed at a temperature ranging between 160° C. and 240° C.

5. A sensor for moisture in an atmosphere as recited in claim 3 wherein said polymer is polysulfon annealed at a temperature ranging between 140° C. and 200° C.

6. A sensor for moisture in an atmosphere as recited in claim 1 wherein said polymer has a glass transition temperature greater than 100° C. and a melting point greater than 150° C.

7. A sensor for moisture in an atmosphere as recited in claim 1 wherein said polymer has a volume resistivity greater than $10^{14}$ Ohms per centimeter.

8. A sensor for moisture in an atmosphere as recited in claim 1 wherein said polymer has a dielectric breakdown strength greater than 14 kilovolts per millimeter.

9. A sensor for moisture in an atmosphere as recited in claim 1 wherein said polymer has a thermal deflection temperature under load above 120° C. and a resistance to heat temperature above 100° C.

10. A sensor for sensing moisture in an atmosphere comprising in combination:
    a first conductor;
    a film disposed on said first conductor composed principally of a polymer with a water sorption capacity in a range between 10 and 40 milligrams of water per gram of polymer at a temperature of 30° C. and a relative humidity of 90% RH;
    a second conductor disposed on said film; and
    means to couple said first and second conductors to a source of electrical energy whereby the moisture in said atmosphere can be sensed by detecting a change in an electrical property of said film.

11. A sensor for sensing moisture in an atmosphere as recited in claim 10 wherein said electrical property is an electrical capacitance of said film.

12. A sensor for sensing moisture in an atmosphere as recited in claim 10 wherein said electrical property is an electrical impedance of said film.

13. A sensor for sensing moisture in an atmosphere as recited in claim 10 wherein said polymer is selected from the group consisting of polyethersulfon and polysulfon.

14. A sensor for sensing moisture in an atmosphere as recited in claim 13 wherein said polymer is polyethersulfon annealed at a temperature ranging between 160° C. and 240° C.

15. A sensor for sensing moisture in an atmosphere as recited in claim 13 wherein said polymer is polysulfon annealed at a temperature ranging between 140° C. and 200° C.

16. A sensor for sensing moisture in an atmosphere as recited in claim 10 wherein said polymer has a glass transition temperature greater than 100° C. and a melting point greater than 150° C.

17. A sensor for sensing moisture in an atmosphere as recited in claim 10 wherein said polymer has a volume resistivity greater than $10^{14}$ Ohms per centimeter.

18. A sensor for sensing moisture in an atmosphere as recited in claim 10 wherein said polymer has a dielectric breakdown strength greater than 14 kilovolts per millimeter.

19. A sensor for sensing moisture in an atmosphere as recited in claim 10 wherein said polymer has a thermal deflection temperature under load above 120° C. and a resistance to heat temperature above 100° C.

* * * * *